US008816309B1

(12) United States Patent
Struthers et al.

(10) Patent No.: US 8,816,309 B1
(45) Date of Patent: Aug. 26, 2014

(54) RADIATION SHIELDING PANEL

(71) Applicant: Manticore International, LLC, Hiram, OH (US)

(72) Inventors: Clayton W. Struthers, Hiram, OH (US); John P. Creamer, Garrettsville, OH (US); Dennis D. Loyd, Liberty Township, OH (US)

(73) Assignee: Manticore International, LLC, Hiram, OH (US)

( * ) Notice: Subject to any disclaimer, the term of this patent is extended or adjusted under 35 U.S.C. 154(b) by 0 days.

(21) Appl. No.: 13/740,912

(22) Filed: Jan. 14, 2013

Related U.S. Application Data

(60) Provisional application No. 61/586,534, filed on Jan. 13, 2012.

(51) Int. Cl.
*G21F 3/00* (2006.01)

(52) U.S. Cl.
CPC ........................................ *G21F 3/00* (2013.01)

USPC ...................................... 250/515.1; 250/519.1

(58) Field of Classification Search
USPC .............................................. 250/515.1, 519.1
See application file for complete search history.

(56) References Cited

U.S. PATENT DOCUMENTS

| 6,048,379 | A  | * | 4/2000  | Bray et al.    | ...................... | 75/229    |
| 6,517,774 | B1 | * | 2/2003  | Bray et al.    | ...................... | 419/65    |
| 6,635,893 | B2 | * | 10/2003 | O'Kane et al.  | ............. | 250/506.1 |

* cited by examiner

*Primary Examiner* — Kiet T Nguyen
(74) *Attorney, Agent, or Firm* — Calfee, Halter & Griswold LLP

(57) ABSTRACT

A radiation shielding panel includes a tungsten powder and a polyurea material. The tungsten powder includes tungsten particles having three different specific diameters. The tungsten powder is mixed and dispersed into the polyurea material. The mixture of the polyurea material and the tungsten powder shields radiation greater than about 6 MeV.

18 Claims, 5 Drawing Sheets

US 8,816,309 B1

RADIATION SHIELDING PANEL

This application claims the benefit of U.S. Provisional Application No. 61/586,534, filed Jan. 13, 2012, which is hereby fully incorporated by reference.

BACKGROUND

The present invention relates to radiation shielding from Gamma and X-Ray sources (Gamma). It finds particular application in conjunction with using different sizes of material to obtain shielding at reduced thickness and/or total weight per unit volume. It will be appreciated, however, that the invention is also amenable to other applications and will be described with particular reference thereto.

Current regulatory and environmental concerns and events worldwide have created an emergent need for a more effective radiation shield that may be deployed in previously unrecognized fashions. Man made and natural disasters are at an all time high. From earthquakes and blasts, to dirty bombs, and nuclear weapons (radiation), it is evident that there is a need for protective materials that cover a multitude of varying radiological threat assessments and environments. Many products have been invented with a common goal of protecting human life and infrastructure. It should be further stated that environmental impact is a consideration in new infrastructure development and product manufacturing.

Products such as concrete, lead, and steel coatings have been used in various applications to protect human life and infrastructure from ionizing radiation. The use of lead and/or concrete, for example, for protection against multi-spectral-radiations has resulted in ecological debates regarding the creation and disposal of lead based products.

The present invention provides a new and improved apparatus and method which addresses the above-referenced problems.

SUMMARY

In one embodiment, a radiation shielding panel includes a tungsten powder and a polyurea material. The tungsten powder includes tungsten particles having three different specific diameters. The tungsten powder is mixed and dispersed into the polyurea material. The mixture of the polyurea material and the tungsten powder shields radiation greater than about 6 MeV.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

DETAILED DESCRIPTION OF ILLUSTRATED EMBODIMENT

Figures 1, 2:
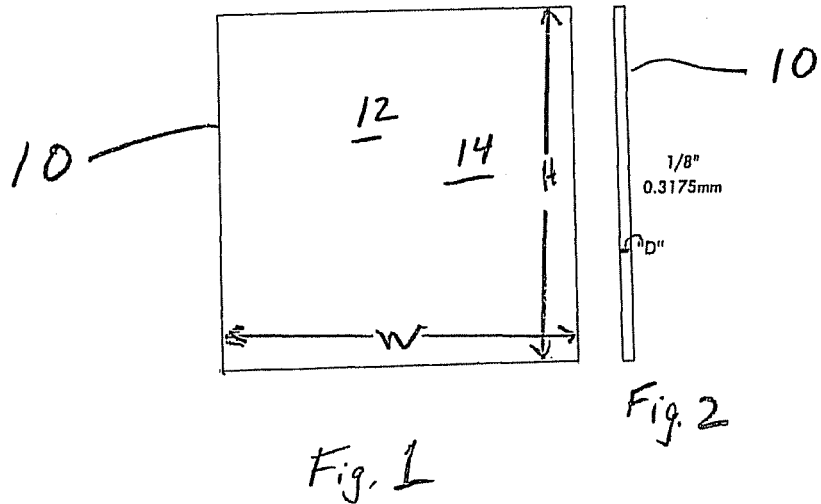
FIG. 1 illustrates a schematic representation of a front view of a panel in accordance with one embodiment of an apparatus illustrating principles of the present invention.
FIG. 2 illustrates a schematic representation of a side view of the panel of FIG. 1 in accordance with one embodiment of an apparatus illustrating principles of the present invention.

With reference to FIGS. 1 and 2, a simplified component diagram of an exemplary wall panel 10 is illustrated in accordance with one embodiment of the present invention. In the illustrated embodiment, the panel 10 includes one (1) layer.

The layer is a combination of an "A" component 12 (e.g., "A" side") and a "B" component 14 (e.g., "B" side"). In one embodiment, the A component 12 includes an accelerant, and the B component 14 represents a main body of the panel 10 and includes a polyurea mixture (polyurea material). The panel 10 is made by combining the A component 12 and the B component 14 with a particle mixture of tungsten. In one embodiment, the mixture of tungsten particles is a tungsten powder. The A component 12, the B component 14, and the particle mixture of tungsten powder are then poured into a form and allowed to cure. In one embodiment, the main body 14 of the panel 10 is HM-VK™ ultra high strength handmix polyurea elastomer.

Figure 3:
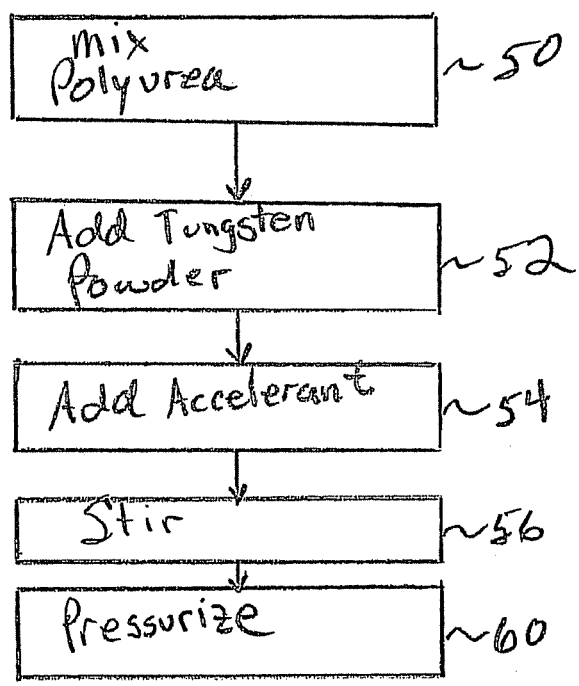
FIG. 3 is an exemplary methodology of manufacturing a panel in accordance with one embodiment illustrating principles of the present invention.

With reference to FIGS. 1-3, during a first phase, in a step 50, the B component 14 polyurea mixture of a predetermined amount (e.g., about 20 lbs. to about 25 lbs. of the Tungsten powder and about 75 ounces to about 83 ounces of the "B" component (e.g., HM-VK™)) is placed into a mixing apparatus and stirred, by itself, for about 1 minute to about 4 minutes. In a step 52, the mixture of tungsten powder is slowly added to the polyurea mixture. The tungsten powder and the polyurea mixture are stirred together for an additional time (e.g., between about 1 minute and about 4 minutes), during which time the tungsten powder is dispersed in the polyurea mixture and the polyurea mixture and the tungsten powder mixture begin to slightly thicken into the B component 14 material. When the polyurea mixture and the tungsten powder mixture have sufficiently thickened into the B component 14 material, (e.g., after the additional stirring time of between about 1 minute and about 4 minutes), in a step 54 the A component 12 material (e.g., accelerant) is added. In one embodiment, about 20 ounces to about 25 ounces of the "A" component HM-VK™ accelerant is added in the step 54. Adding the A component 12 material causes a long chain polymer mixture to rapidly setup. The exemplary amounts of the A component 12 and the B component 14 discussed in the present paragraph have been found to result in a panel 10 of about 31.875" by about 31.875" by about 0.125" thick.

After about 4 minutes of stirring the combined A component 12 (e.g., the accelerant) and the B component 14 (e.g., the main panel body including the polyurea mixture and the tungsten powder mixture) in a step 56, the combined material is poured into a form and pressurized in a step 60. In one embodiment, the combined material is pressurized to about 6,000 psi for between about 4 hours and 4½ hours.

After about the first seven (7) minutes of the about 4 (four) hour pressurization, the combined A component 12 and B component 14 material enters a first transitional phase (e.g., the t-phase). Then, over the remainder of the 4 hour press time (e.g., after reaching the first t-phase), the panel material attains the physical characteristics of heavy rubber. The material state during and after mixing represents numerous applications in manufacturing and emergency radiological mitigation. It is noted that the A component 12 (e.g., the accelerant) vaporizes during the four (4) hour pressurization.

Companies such as, but not limited to, ArmorThane, LineX, and Specialty Products Inc. (SPI) have produced Urethane products/Polyurea products. As stated by the Polyurea Development Association, the advantages and benefits of Polyurea include: no volatile organic compounds (VOC's) and little to no odor, some systems are USDA and potable approved; weather tolerant (cures at about 25° F. to greater than about 300° F., even in high humidity); excellent resistance to thermal shock; flexible; bridges cracks; waterproof, seamless and resilient; unlimited mil thickness in one application; spray, hand mix, and caulk grade materials; excellent bond strengths to properly prepared substrates; resistant to various solvents, caustics, and mild acids; and low permeability, excellent sustainability.

| Material List | |
|---|---|
| Polyurea B component | about 9% to about 30% by volume |
| Tungsten Powder | about 70% to about 93% by volume |
| A component | about 25% to about 30% of B component by volume |

The percentages listed above are merely examples and, furthermore, may vary slightly for many reasons to include, but are not limited to, ambient temperature, variations in the materials used, water content, radiation shielding requirements etc.

In one embodiment, the tungsten powder includes a plurality of different sized particles.

Figure 4:
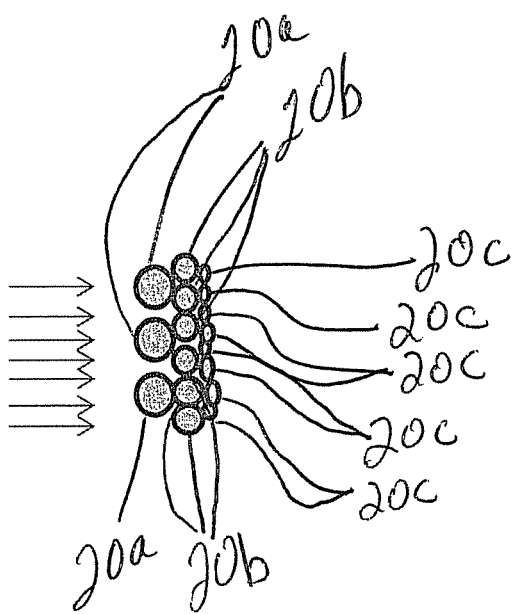
FIG. 4 illustrates a schematic representation of different sized particles of tungsten powder in a panel in accordance with one embodiment of an apparatus illustrating principles of the present invention.

In one embodiment, the tungsten powder includes three (3) differently sized particles. For example, the three (3) differently sized particles have diameters of about 90.0 microns, about 9.0 microns, and about 0.9 microns. In one example, the tungsten powder includes, by volume, about 80% of tungsten particles having a diameter of about 90.0 microns, about 15% of tungsten particles having a diameter of about 9.0 microns, and about 5% of tungsten particles having a diameter of about 0.9 microns. With reference to FIG. 4, the largest sized particles 20*a* (e.g., having a diameter of about 90.0 microns) establishes a base layer and then smaller sizes 20*b* (e.g., having a diameter of about 9.0 microns) and 20*c* (e.g., having a diameter of about 0.9 microns) fill in the gaps between the largest size so that final product has less weight, while providing significant shielding to radiation greater than about 6 million-electron volts (MeV), when compared to conventional materials (e.g., lead, steel, and concrete).

Gamma radiation is a hazard from multiple sources including, but not limited to, nuclear weapons, mixed nuclear waste, and others. In one embodiment of the present invention, gamma radiation exposure is reduced by incorporating a shielding material, which is in the form of the panel 10 described above, that absorbs a wide variety of radiation from various gamma emitting sources. Various high atomic weight materials (e.g., concrete, steel, lead, tungsten, depleted uranium, etc.) have been used for gamma radiation shielding. In one embodiment, it is contemplated that the proprietary gamma radiation shielding materials and gamma radiation absorbers are incorporated into the polyurea layer to reduce or minimize gamma radiation penetration in the panel 10.

Figures 5, 6:
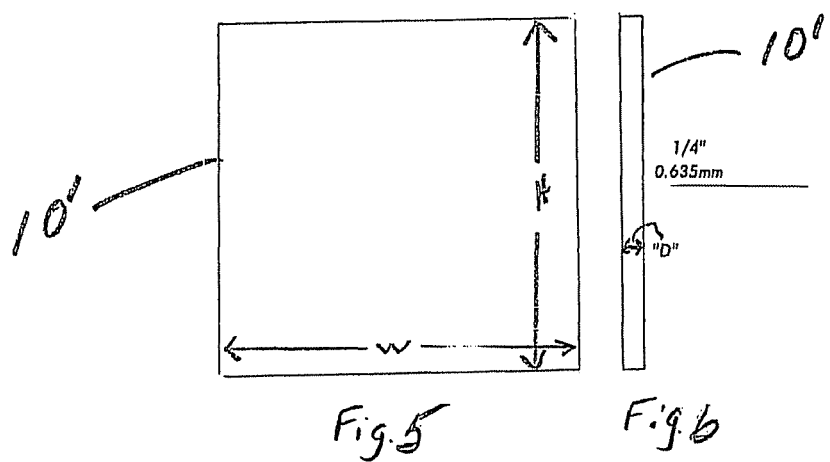
FIG. 5 illustrates a schematic representation of a front view of a second panel in accordance with one embodiment of an apparatus illustrating principles of the present invention.
FIG. 6 illustrates a schematic representation of a side view of the panel of FIG. 5 in accordance with one embodiment of an apparatus illustrating principles of the present invention.

It is contemplated that the panel 10 as shown in FIGS. 1 and 2 is about 30" wide (see "W" in FIG. 1) by about 30" high (see "H" in FIG. 1) with a thickness (e.g., depth) of about ⅛" (see "D" in FIG. 2). The panel 10 includes between about 78% and about 92% of the tungsten powder and between about 8% and about 22% of the polyurea material. A panel 10' illustrated in FIGS. 5 and 6 is about 30" wide (see "W" in FIG. 5) by about 30" high (see "H" in FIG. 5) with a thickness (e.g., depth) of about ¼" (see "D" in FIG. 6). The panel 10' includes between about 80% and about 90% of the tungsten powder and between about 10% and about 20% of the polyurea material.

Such panel measurements are in accordance with ANSI 42.46 For Determination of Imaging Performance of X-Ray and Gamma Ray Systems for Cargo and Vehicle Screening. With reference to FIGS. 1, 2, 5, and 6, it is contemplated that a panel 10 having a thickness of about ⅛" has a density of about 5.06 g/cm$^3$, and that a panel 10' having a thickness of about ¼" has a density of about 5.12 g/cm$^3$.

Testing has shown that the panel 10 having a mean thickness of about ⅛" offers radiation shielding (e.g., gamma radiation shielding) equivalent to a steel sheet having a mean thickness of about 0.38004". Testing has also shown that the panel 10' having a mean thickness of about ¼" thick offers radiation shielding (e.g., gamma radiation shielding) equivalent to a steel sheet having a thickness about 0.657907".

The panel 10 includes multiple components of polyurea and tungsten and protects against multiple ionizing radiation sources. The panel 10 may be referred to as a single layer, ionizing radiation shield panel (e.g., a multi-spectral ionizing radiation panel (MSIRP) panel), including the plurality of different sized particles. It is contemplated that the panel 10 is non-structural, allowing it to be manufactured in multiple shapes and sizes to accommodate retrofitting on existing structures (e.g., embassies, federal installations, perimeter structures, refineries, etc). A non-structural panel 10 is not part of the structure of the building and maybe used as an after-market product (or addition) to the structure. The panel 10 may be described as a monolithic-like structure.

Figure 7:
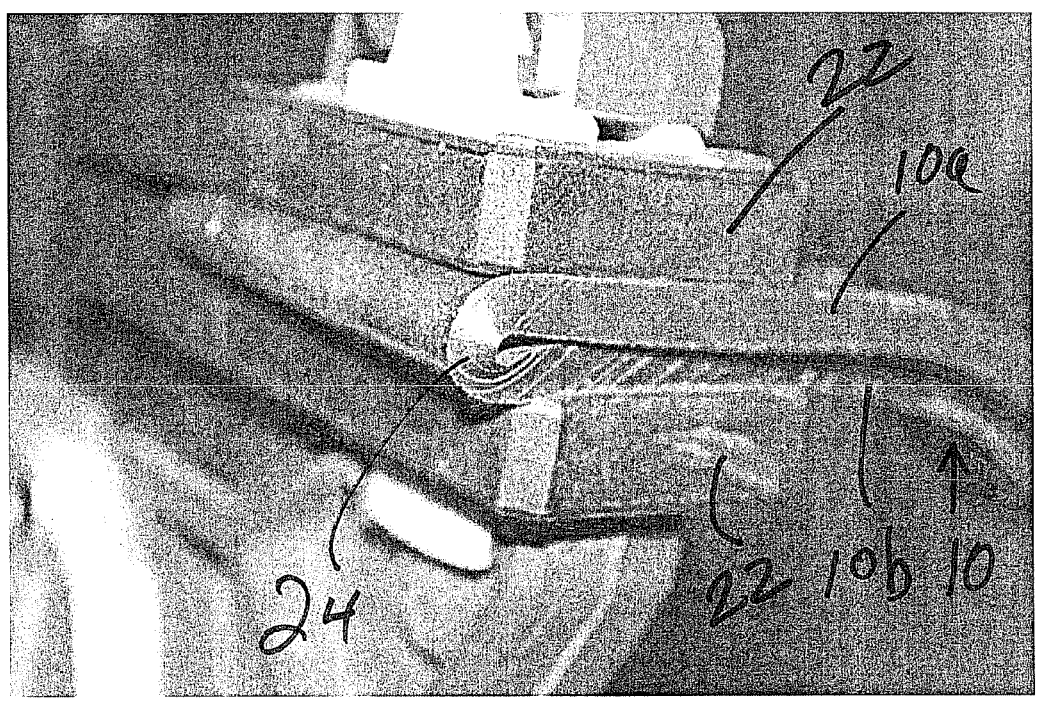
FIG. 7 illustrates a schematic representation of a panel in a clamp to show how pliable the panel is in accordance with one embodiment of an apparatus illustrating principles of the present invention.
Figure 8:
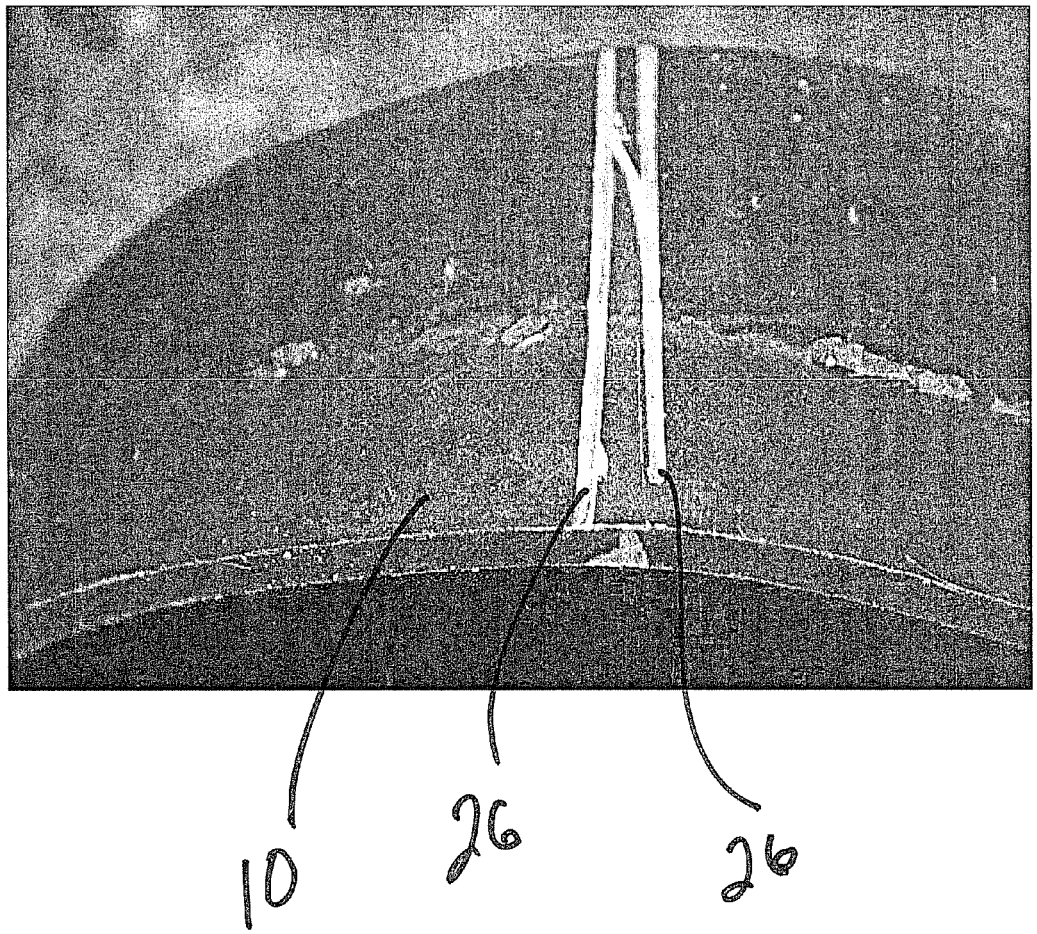
FIG. 8 illustrates a schematic representation of the panel of FIG. 7 after being released from the clamp in accordance with one embodiment of an apparatus illustrating principles of the present invention.

The panel 10 is also pliable. As illustrated in FIG. 7, in one embodiment, one side 10*a* of the panel 10 is folded to be adjacent a second side 10*b* of the panel 10 with a clamp 22 exerting pressure of about 600 lbs./in$^2$ proximate to a fold 24 created in the panel 10. FIG. 8 illustrates the panel 10 of FIG. 7 after being held in the clamp 22 (see FIG. 7) for about 24 hours and then removed. Two (2) lines 26 on the panel 10 approximately illustrate the position of the fold 24. FIG. 8 illustrates the pliability of the panel 10, since the panel 10 includes no cracking or fatigue at the fold 24 even after being held in the clamp 22 under about 600 lbs./in$^2$ for about 24 hours.

It is contemplated that a properly formulated panel 10, when secured adequately to a structure or testing apparatus, will withstand at least:

1. Most levels of ionizing gamma radiation (about 100 electron volts (eV) to above about 6 MeV).
2. Shock and related stressor's.

The panel 10, as described above with reference to FIGS. 1, 2, and 5-7 is designed and engineered to absorb and block ionizing radiations across the spectrum from about 10 electron Volts to about 6 MeV and to protect human life and infrastructure. The panel 10 also offers flexibility in engineering and design so that panel dimensions and thickness may be adjusted to meet various radiological environments and situations based on consumer and manufacturing demands.

In addition, the panel 10, as described above, is designed for a broad range of multi-purpose uses. For example, the panel 10 materials in their liquid state, may be sprayed and applied by conventional methods for providing protection for nuclear based applications ranging from nuclear power plants, medical, radiological laboratories and other locations such as military applications and also for homeland security. Still other uses would include substitution for traditional lead shielding in commodities including x-ray machines, medical radiology suites and others.

In each of these uses, the concept is to provide significant protection for employees from the effects of crime, terrorism or warfare. The potential threats from small arms, car bombs and improvised devices which might include radiation dispersal devices are the most likely security and military based use.

The end result of using this material is that a wide range of protections are available from the same material (e.g., the panel 10). In one embodiment, the panel 10 shields radiation greater than about 6 MeV.

Tungsten and polyurea have not been used in radiation shielding mix designs, primarily due to the inherent cost of pure ore. In the embodiments of the present invention, we have tested and categorically shown that better gamma radiation shielding can be attained using tungsten powder, in lieu of relatively expensive sheets of tungsten—a recent test we have conducted confirms this. During the curing process, the panel material in the press reaches the first t-phase relatively rapidly (e.g., in minutes). Then, as noted above, over the remainder of the 4 hour press time (e.g., after reaching the first t-phase), the panel material attains the physical characteristics of heavy rubber.

Overpressure from explosives, chemical, mechanical and other events are often the part of an event with the greatest hazard. The panel 10 provides protection for people or systems (e.g., an office and/or electronic equipment) to enhance survivability. By coupling several kinds of protection, from ionizing radiation and radio frequency radiation, the panel 10 described above fulfills several requirements for security and protection simultaneously and in a new and unique way.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A radiation shielding panel, comprising:
    a tungsten powder including tungsten particles having three different specific diameters; and
    a polyurea material, the tungsten powder being mixed and dispersed into the polyurea material, the mixture of the polyurea material and the tungsten powder shields radiation greater than about 6 MeV.

2. The radiation shielding panel as set forth in claim 1, wherein:
    the three different specific diameters of the tungsten particles are about 0.9 microns, about 9.0 microns, and about 90.0 microns.

3. The radiation shielding panel as set forth in claim 2, wherein:
    about 5% of the powdered tungsten is the tungsten particles having diameters of about 0.9 microns;
    about 15% of the powdered tungsten is the tungsten particles having diameters of about 9.0 microns; and
    about 80% of the powdered tungsten is the tungsten particles having diameters of about 90.0 microns.

4. The radiation shielding panel as set forth in claim 1, wherein:
    the panel includes ≥ about 70% and about 90% of the tungsten powder; and
    the panel includes ≤ about 10% and about 30% of the polyurea material.

5. The radiation shielding panel as set forth, in claim 4, wherein:
    the panel is about 1/8" thick;
    the panel includes between about 80% and about 90% of the tungsten powder; and
    the panel includes about 10% and about 20% of the polyurea material.

6. The radiation shielding panel as set forth in claim 4, wherein:
    the panel is about 1/4" thick;
    the panel includes between about 80% and about 90% of the tungsten powder; and
    the panel includes about 10% and about 20% of the polyurea material.

7. A radiation shielding panel, comprising:
    a tungsten powder including tungsten particles having three different specific diameters of about 0.9 microns, about 9.0 microns, and about 90.0 microns; and
    a polyurea material, the tungsten powder being mixed and dispersed into the polyurea material, the panel being pliable without cracks when a first side of the panel is folded to be adjacent a second side of the panel.

8. The radiation shielding panel as set forth in claim 7, wherein:
    the mixture of the polyurea material and the tungsten powder shielding radiation greater than about 6 MeV.

9. The radiation shielding panel as set forth in claim 7, wherein:
    about 5% of the powdered tungsten is the tungsten particles having diameters of about 0.9 microns;
    about 15% of the powdered tungsten is the tungsten particles having diameters of about 9.0 microns; and
    about 80% of the powdered tungsten is the tungsten particles having diameters of about 90.0 microns.

10. The radiation shielding panel as set forth in claim 7, wherein:
    the panel includes ≥ about 70% and about 90% of the tungsten powder; and
    the panel includes ≤ about 10% and about 30% of the polyurea material.

11. The radiation shielding panel as set forth in claim 10, wherein:
    the panel is about 1/8" thick;
    the panel includes between about 80% and about 90% of the tungsten powder; and
    the panel includes about 10% and about 20% of the polyurea material.

12. The radiation shielding panel as set forth in claim 10, wherein:
    the panel is about 1/4" thick;
    the panel includes between about 80% and about 90% of the tungsten powder; and
    the panel includes about 10% and about 20% of the polyurea material.

13. A method of forming a radiation shielding panel, the method including:
   forming a tungsten powder mixture including tungsten particles having three different specific diameters;
   mixing a polyurea with the tungsten powder mixture;
   adding an accelerant to the polyurea and tungsten powder mixture; and
   pressurizing the accelerant, polyurea, and tungsten powder mixture at about 6,000 lbs/in$^2$ for between about 4 hours and about 4½ hours.

14. The method of forming a radiation shielding panel as set forth in claim wherein claim 13, wherein the step of mixing the polyurea and tungsten powder mixture includes:
   mixing the polyurea and the tungsten powder mixture for between about 4 minutes and about 7 minutes.

15. The method of forming a radiation shielding panel as set forth in claim 13, further including:
   forming the panel to about 30" high by about 30" wide by ⅛" thick.

16. The method of forming a radiation shielding panel as set forth in claim 13, wherein the step of forming the tungsten powder mixture includes:
   preparing the tungsten powder mixture to include the three different sized tungsten particles having, by volume, about 80% of tungsten particles having a diameter of about 90.0 microns, about 15% of tungsten particles having a diameter of about 9.0 microns, and about 5% of tungsten particles having a diameter of about 0.9 microns.

17. The method of forming a radiation shielding panel as set forth in claim 13, wherein the step of adding the accelerant includes:
   mixing the accelerant into the polyurea and tungsten powder mixture for about 4 minutes.

18. The method of forming a radiation shielding panel as set forth in claim 17, wherein the step of forming the polyurea and tungsten powder mixture includes:
   mixing the polyurea and tungsten powder mixture for between about 4 minutes and about 7 minutes.

\* \* \* \* \*